(12) United States Patent
Hassan et al.

(10) Patent No.: US 8,034,970 B2
(45) Date of Patent: Oct. 11, 2011

(54) METHOD OF MAKING PHTHALIC ACID DIESTERS

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 333 days.

(21) Appl. No.: 12/144,296

(22) Filed: Jun. 23, 2008

(65) Prior Publication Data

US 2009/0005587 A1 Jan. 1, 2009

Related U.S. Application Data

(60) Provisional application No. 60/946,505, filed on Jun. 27, 2007.

(51) Int. Cl.
*C07C 67/08* (2006.01)

(52) U.S. Cl. ............... 560/99; 560/76; 560/96; 560/98

(58) Field of Classification Search .................. None
See application file for complete search history.

(56) References Cited

U.S. PATENT DOCUMENTS

| | | | |
|---|---|---|---|
| 3,879,444 A | | 4/1975 | Fujita et al. |
| 4,675,434 A | * | 6/1987 | Uhm et al. .................. 560/99 |
| 5,877,350 A | | 3/1999 | Langer et al. |
| 6,241,472 B1 | * | 6/2001 | Bosch et al. ............... 415/208.3 |
| 6,368,366 B1 | | 4/2002 | Langer et al. |
| 6,368,367 B1 | | 4/2002 | Langer et al. |
| 6,383,237 B1 | * | 5/2002 | Langer et al. ............... 44/301 |
| 6,866,411 B1 | * | 3/2005 | Stelzer et al. ............... 366/136 |
| 7,461,970 B2 | | 12/2008 | Brown |
| 2003/0043690 A1 | | 3/2003 | Holl |
| 2004/0052158 A1 | | 3/2004 | Holl |
| 2005/0033069 A1 | | 2/2005 | Holl et al. |
| 2008/0144431 A1 | * | 6/2008 | Troxler .................. 366/164.1 |
| 2009/0323458 A1 | | 12/2009 | Fischer et al. |

FOREIGN PATENT DOCUMENTS

| | | |
|---|---|---|
| JP | 08-104662 A | 4/1996 |
| JP | 11-246486 A | 9/1999 |

OTHER PUBLICATIONS

Office Action Dated Jul. 28, 2010 for US U.S. Appl. No. 12/635,433.

* cited by examiner

*Primary Examiner* — Sudhakar Katakam
(74) *Attorney, Agent, or Firm* — Porter Hedges LLP; Timothy S. Westby

(57) ABSTRACT

Methods and systems for the production of phthalic acid diesters are described herein. The methods and systems incorporate the novel use of a high shear device to promote dispersion and mixing of a phthalic acid derivative with alcohol. The high shear device may allow for lower reaction temperatures and pressures and may also reduce reaction time with existing catalysts.

14 Claims, 2 Drawing Sheets

METHOD OF MAKING PHTHALIC ACID DIESTERS

CROSS-REFERENCE TO RELATED APPLICATIONS

This application claims the benefit under 35 U.S.C. §119 (e) of U.S. Provisional Patent Application No. 60/946,505, filed Jun. 27, 2007, the disclosure of which is hereby incorporated herein by reference.

STATEMENT REGARDING FEDERALLY SPONSORED RESEARCH OR DEVELOPMENT

Not Applicable.

BACKGROUND

1. Field of the Invention

This invention relates generally to the field of chemical reactions. More specifically, the invention relates to methods of making diester phthalates incorporating high shear mixing.

2. Background of the Invention

Plasticizers are widely used in many ways in plastics, coating compositions, sealing compositions and rubber articles. They interact physically with thermoplastic high polymers without reacting chemically, preferably by means of their solvent and swelling capability. This forms a homogeneous system whose thermoplastic range has been shifted to lower temperatures compared to the original polymer, with the result that, for example, the ability to change shape and the elasticity are increased and the hardness is reduced.

To open up very wide fields of application for plasticizers, they have to fulfill a number of requirements. In the ideal case, they should be odorless, colorless, light-resistant, cold-resistant and heat-resistant. In addition, it is expected that they are resistant to water, do not burn readily, have a low volatility and are not harmful to health. Furthermore, the preparation of the plasticizers should be simple and, to meet ecological demands, should be carried out without producing waste materials such as by-products which cannot be recycled and wastewater containing pollutants.

Among the most important plasticizers are the esters of dicarboxylic and polycarboxylic acids with plasticizer alcohols, i.e. unbranched or branched primary alcohols having from about 6 to 13 carbon atoms, which can be used as individual compounds or as a mixture. The preparation of the esters has been carried out by the classical process by reacting the acids or acid anhydrides with an alcohol or a mixture of different alcohols in the presence of an acid, preferably sulfuric acid, as catalyst. The alcohol component is usually used in excess. Attempts have been made to counter adverse color and odor of the reaction product by targeted selection of the acid used as catalyst, by mild reaction conditions and by complicated purification measures.

A further development in the preparation of esters suitable as plasticizers constitutes the use of metal-containing esterification catalysts. Suitable catalysts are, for example, tin, titanium and zirconium which are used as finely divided metals or advantageously in the form of their salts, oxides or soluble organic compounds. These catalysts are high-temperature catalysts which reach their full activity only at esterification temperatures above 180° C. Examples are tin powder, tin(II) oxide, tin(II) oxalate, titanate esters such as tetraisopropyl orthotitanate or tetrabutyl orthotitanate and also zirconium esters such as tetrabutyl zirconate. Alkyl titanates and titanium chelates, i.e. titanates of polyalcohols, have achieved particular importance in industrial production processes.

Furthermore, another process for the esterification of phthalic anhydride involves reaction with isodecanol in the presence of tetrabutyl titanate as catalyst at 230° C. Subsequent to the esterification, the reaction mixture is treated with sodium carbonate solution and the excess alcohol is distilled off. The treatment with the sodium carbonate solution neutralizes the phthalic monoesters present in the reaction mixture to form the corresponding salts. These salts are obtained as a slimy precipitate which can be filtered off only with difficulty, necessitating a high outlay in terms of time and apparatus. Obtaining the desired phthalic diester in pure form is thus associated with considerable difficulties. The modern processes for preparing ester plasticizers thus do not yet fulfill all aspects of the above-described demands made of the production process and the reaction product.

Consequently, there is a need for accelerated methods for esterification by improving the mixing of alcohol into the phthalic acid derivative phase.

SUMMARY

Methods and systems for the esterification of phthalic acid and its derivatives are described herein. The methods and systems incorporate the novel use of a high shear device to promote dispersion and solubility of alcohol in the phthalic acid and/or derivative. The high shear device may allow for lower reaction temperatures and pressures and may also reduce esterification time. Further advantages and aspects of the disclosed methods and system are described below.

In an embodiment, a method of making a phthalic acid diester comprises introducing an alcohol into a phthalic acid derivative stream to form a reactant stream. The method also comprises subjecting the reactant stream to a shear rate of greater than about 20,000 $s^{-1}$ with a high shear device. In addition, the method comprises contacting the reactant stream with a catalyst to make the phthalic acid diester.

In an embodiment, a system for producing a phthalic acid diester comprises at least one high shear device for mixing an alcohol and a phthalic acid derivative comprising a rotor and a stator. The rotor and the stator are separated by a shear gap in the range of from about 0.02 mm to about 5 mm. The shear gap is a minimum distance between the rotor and the stator. The high shear device is capable of producing a tip speed of the at least one rotor of greater than about 23 m/s (4,500 ft/min). In addition, the system comprises a pump configured for delivering a liquid stream to the high shear device. The system also comprises a reactor for esterifying the phthalic acid derivative coupled to the high shear device. The reactor is configured for receiving high-shear treated stream from said high shear device.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION

Figure 1:
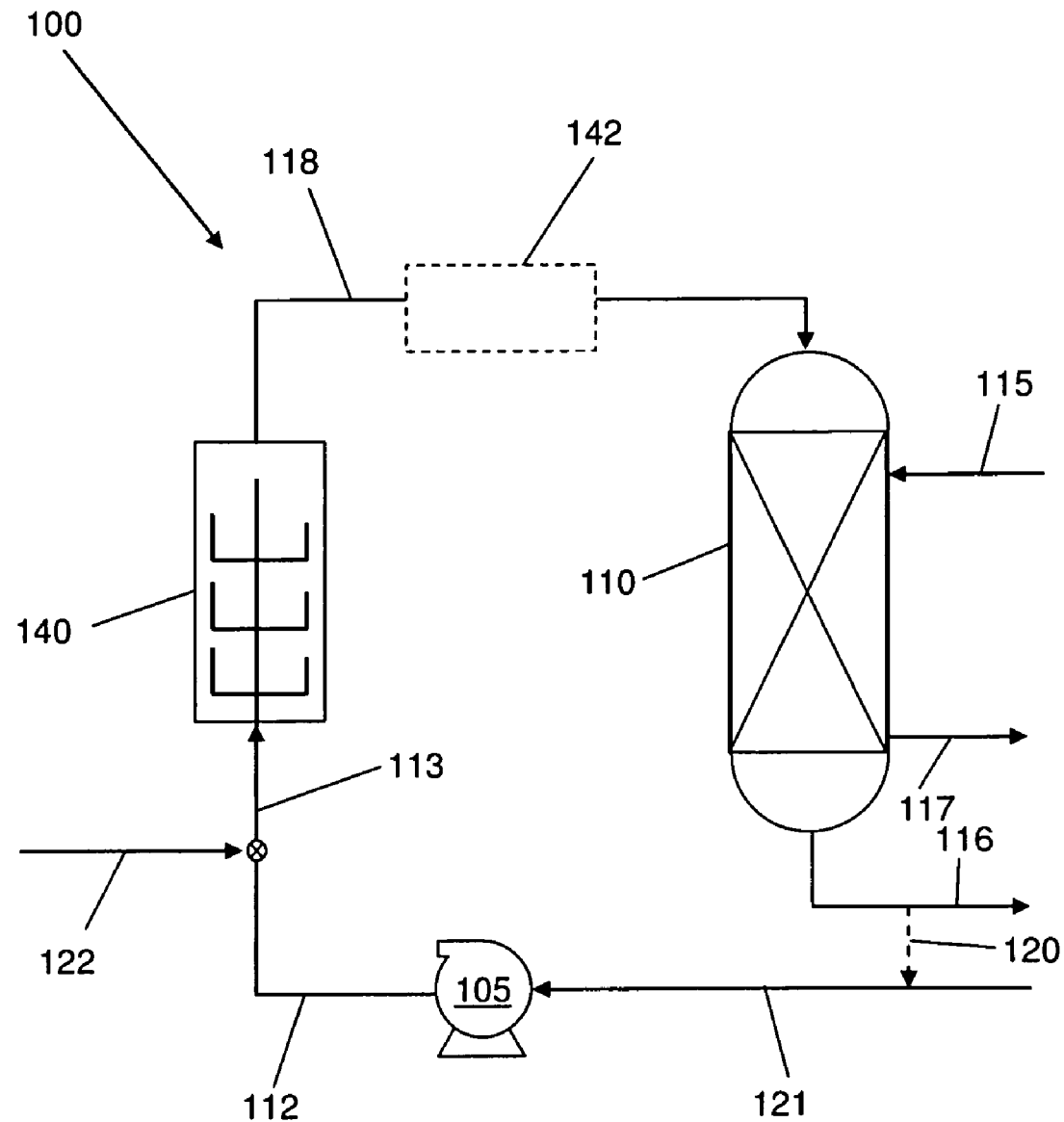
FIG. 1 is a process flow diagram of a process for the production of phthalic acid diesters, according to certain embodiments of the invention.

The disclosed methods and systems for the production of phthalic acid diester comprises utilization of an external high shear mechanical device to provide rapid contact and mixing of an alcohol and a phthalic acid derivative in a controlled environment in the reactor/mixer device. As used herein, "phthalic acid derivative" may refer to any compound derived from phthalic acid including without limitation, phthalic acid, phthalic anhydride, phthaloyl chloride, etc. The high shear device reduces the mass transfer limitations on the reaction and thus increases the overall reaction rate.

Chemical reactions involving liquids, gases and solids rely on time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants. Contact time for the reactants and/or catalyst is often controlled by mixing which provides contact with two or more reactants involved in a chemical reaction. A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes. Homogeneous reactions may also benefit from high shear mixing, as disclosed herein, by at least providing uniform temperature distribution within the reactor and minimizing potential side reactions. Accordingly, in some embodiments, a high shear process as described herein promotes homogeneous chemical reaction(s).

System for the Production of Phthalic Acid Diesters. A high shear phthalic acid diester production system will now be described in relation to FIG. 1, which is a process flow diagram of an embodiment of a high shear system 100 for the production of phthalic acid diesters via the esterification of phthalic acid and its derivatives with an alcohol in the presence of a catalyst dispersed in the liquid phase in a reactor 110. Embodiments of the process are characterized by the use of a high shear device 140 and introduction of alcohol to the phthalic acid or derivative before entering the high shear device 140. Generally, embodiments of the process are carried out by reacting a saturated aliphatic alcohol containing about 1 to about 10 carbon atoms with a phthalic acid derivative such as phthalic acid or phthalic anhydride to obtain the desired diester reaction product.

The basic components of a representative system include external high shear device (HSD) 140, vessel 110, and pump 105. As shown in FIG. 1, the high shear device may be located external to vessel/reactor 110. Each of these components is further described in more detail below. Line 121 is connected to pump 105 for introducing phthalic acid derivative. Line 113 connects pump 105 to HSD 140, and line 118 connects HSD 140 to vessel 110. Line 122 is connected to line 113 for introducing the phthalic acid derivative. Line 117 is connected to vessel 110 for removal of unconverted reactants. Additional components or process steps may be incorporated between vessel 110 and HSD 140, or ahead of pump 105 or HSD 140, if desired.

High shear devices (HSD) such as a high shear device, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 gm. High shear mechanical devices include homogenizers as well as colloid mills.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear device systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy—high shear devices and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m$^3$. In embodiments, the energy expenditure is in the range of from about 3000 W/m$^3$ to about 7500 W/m$^3$. The shear rate generated in a high shear device may be greater than 20,000 s$^{-1}$. In embodiments, the shear rate generated is in the range of from 20,000 s$^{-1}$ to 100,000 s$^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec) =π·D·n, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, 2πR, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear device may be produced during operation. In certain embodiments, the local pressure is at least about 1034 MPa (about 150,000 psi).

Figure 2:
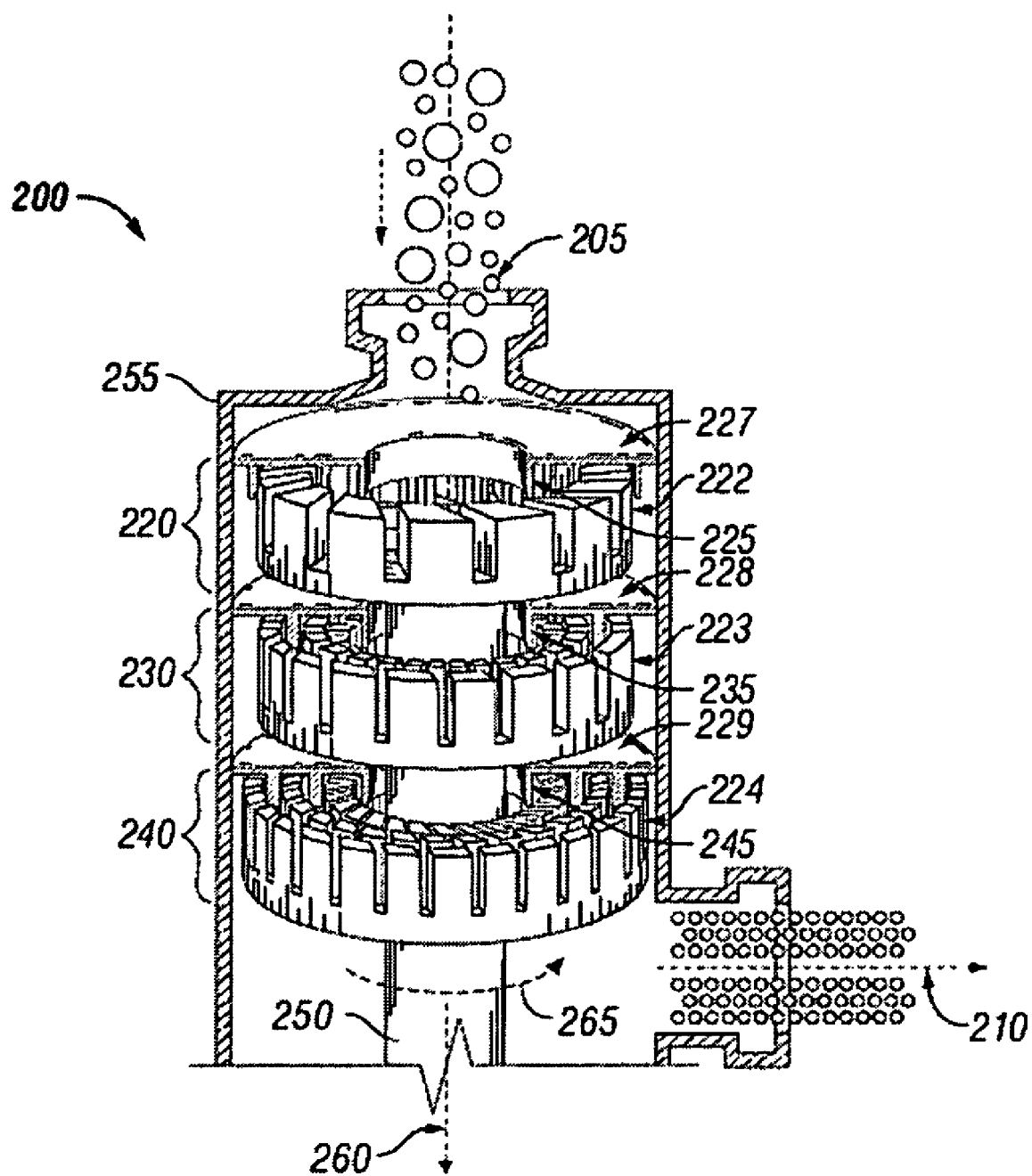
FIG. 2 is a longitudinal cross-section view of a multi-stage high shear device, as employed in an embodiment of the system of FIG. 1.

Referring now to FIG. 2, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. The rotor and the stator may be of any suitable size. In one embodiment, the inner diameter of the rotor is about 64 mm and the outer diameter of the stator is about 60 mm. In other embodiments, the inner diameter of the rotor is about 11.8 cm and the outer diameter of the stator is about 15.4 cm. The rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses discontinuous phases comprising gas bubbles, particles (e.g., solid catalyst), or droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 μm; preferably the bubbles are sub-micron in diameter. In certain instances, the average bubble size is in the range from about 1.0 μm to about 0.1 μm. Alternatively, the average bubble size is less than about 400 nm (0.4 μm) and most preferably less than about 100 nm (0.1 μm).

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 μm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor can comprise a single stage dispersing chamber. The accelerated rate reactor can comprise a multiple stage inline disperser comprising at least 2 stages.

Selection of the high shear device 200 is dependent on throughput requirements and desired particle or bubble size in the outlet dispersion 210. In certain instances, high shear device 200 comprises a DISPAX REACTOR® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ⁄3;4" sanitary clamp, 2 HP power, output speed of 7900 rpm, flow capacity (water) approximately 300 L/h to approximately 700 L/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases such as in homogeneous liquid phase reactions, the high shear device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming).

Vessel. Vessel or reactor 110 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 110 may be a tower reactor, and in others a tubular reactor or multi-tubular reactor. A catalyst inlet line 115 may be connected to vessel 110 for receiving a catalyst solution or slurry during operation of the system.

Vessel 110 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 140 in some embodiments, vessel 110 may serve primarily as a storage vessel in some cases. Although generally less desired, in some applications vessel 110 may be omitted, particularly if multiple high shear devices/reactors are employed in series, as further described below.

Heat Transfer Devices. In addition to the above-mentioned heating/cooling capabilities of vessel 110, other external or internal heat transfer devices for heating or cooling a process stream are also contemplated in variations of the embodiments illustrated in FIG. 1. Some suitable locations for one or more such heat transfer devices are between pump 105 and HSD 140, between HSD 140 and vessel 110, and between vessel 110 and pump 105 when system 1 is operated in multi-pass mode. Some non-limiting examples of such heat transfer devices are shell, tube, plate, and coil heat exchangers, as are known in the art.

Pumps. Pump 105 is configured for either continuous or semi-continuous operation, and may be any suitable pumping device that is capable of providing greater than 2 atm pressure, preferably greater than 3 atm pressure, to allow controlled flow through HSD 140 and system 1. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of the pump comprise stainless steel. In some embodiments of the system, pump 105 is capable of pressures greater than about 20 atm. In addition to pump 105, one or more additional, high pressure pump (not shown) may be included in the system illustrated in FIG. 1. For example, a booster pump, which may be similar to pump 105, may be included between HSD 140 and vessel 110 for boosting the pressure into vessel 110. As another example, a supplemental feed pump, which may be similar to pump 105, may be included for introducing additional reactants or catalyst into vessel 110.

Production of Phthalic Acid Diesters. In operation for the production of phthalic acid diester, a method comprises introducing an alcohol into system 100 via line 122, into a phthalic acid derivative stream 112. Alternatively, the alcohol may be fed directly into HSD 140. Pump 105 is operated to pump the phthalic acid derivative stream through line 121, and to build pressure and feed HSD 140, providing a controlled flow throughout high shear device (HSD) 140 and high shear system 100.

In a preferred embodiment, alcohol may continuously be fed into the phthalic acid derivative stream 112 to form reactant stream 113. In high shear device 140, the alcohol and phthalic acid derivative are highly mixed such that nanobubbles and/or microbubbles are formed for superior dissolution of alcohol into solution. Once dispersed, the reaction stream may exit high shear device 140 at high shear device outlet line 118. Stream 118 may optionally enter fluidized or fixed bed 142 in lieu of a slurry catalyst process. However, in a slurry catalyst embodiment, high shear outlet stream 118 may directly enter reactor 110 for reaction. The reaction stream may be maintained at the specified reaction temperature, using cooling coils in the reactor 110 to maintain reaction temperature. Reaction products (e.g. phthalic acid diester) may be withdrawn in the form of vapors at product stream 116.

In embodiments, the phthalic acid diester produced may have the following formula:

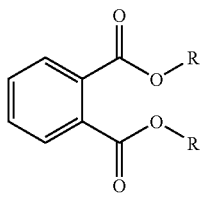

where R is an alkyl group having from 1 to 10 carbon atoms and R may be branched or unbranched.

While embodiments of the process are particularly concerned with the production of the highly advantageous diesters of phthalic acid and its derivatives which are required in large quantities for use as plasticizers for organic polymers such as polyvinyl chloride, the disclosed process may be applicable to the production of esters of suitable aliphatic and other aromatic dicarboxylic acids or anhydrides thereof, for example, maleic anhydride, fumaric acid, and other dicarboxylic acids of the formula:

$$HOOC-(CH_2)_n-COOH$$

in which n denotes a whole number of from 1 to 8, as exemplified by such acids as malonic acid, succinic acid, glutaric acid, adipic acid, pimelic acid, suberic acid, azelaic acid, and sebacic acid. Examples of suitable saturated aliphatic alcohols having about 1 to about 10 carbon atoms are propanol, ethanol, butanol, n-octanol-1, n-octanol-2, 2-ethyl-hexanol-1, n-nonyl alcohol, isodecanol, and decanol.

In an exemplary embodiment, the high shear device comprises a commercial disperser such as IKA® model DR 2000/4, a high shear, three stage dispersing device configured with three rotors in combination with stators, aligned in series. The disperser is used to create the mixture of alcohol and the phthalic acid derivative. The rotor/stator sets may be configured as illustrated in FIG. 2, for example. The combined reactants enter the high shear device via line 113 and enter a first stage rotor/stator combination having circumferentially spaced first stage shear openings. The coarse dispersion exiting the first stage enters the second rotor/stator stage, which has second stage shear openings. The reduced bubble-size dispersion emerging from the second stage enters the third stage rotor/stator combination having third stage shear openings. The dispersion exits the high shear device via line 118. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear device includes a PTFE seal, for example, the seal may be cooled using any suitable technique that is known in the art. For example, the reactant stream flowing in line 113 may be used to cool the seal and in so doing be preheated as desired prior to entering the high shear device.

The rotor of HSD 140 is set to rotate at a speed commensurate with the diameter of the rotor and the desired tip speed. As described above, the high shear device (e.g., colloid mill) has either a fixed clearance between the stator and rotor or has adjustable clearance. HSD 140 serves to intimately mix the reactant liquids (i.e., phthalic acid derivative and alcohol). In some embodiments of the process, the transport resistance of the reactants is reduced by operation of the high shear device such that the velocity of the reaction is increased by greater than a factor of about 5. In some embodiments, the velocity of the reaction is increased by at least a factor of 10. In some embodiments, the velocity is increased by a factor in the range of about 10 to about 100 fold. In some embodiments, HSD 140 delivers at least 300 L/h with a power consumption of 1.5 kW at a nominal tip speed of at least 4500 ft/min (23 m/s), and which may exceed 7900 ft/min (40 m/s). Although measurement of instantaneous temperature and pressure at the tip of a rotating shear unit or revolving element in HSD 140 is difficult, it is estimated that the localized temperature seen by the intimately mixed reactants may be in excess of 500° C. and at pressures in excess of 500 kg/cm$^2$ under high shear conditions. The high shear mixing results in formation of micron or submicron-sized bubbles due to cavitation. In some embodiments, the resultant dispersion has an average bubble size less than about 1.5 μm. Accordingly, the stream exiting HSD 140 via line 118 may comprise micron and/or submicron-sized bubbles. In some embodiments, the mean bubble size is in the range of about 0.4 μm to about 1.5 μm. In some embodiments, the mean bubble size is less than about 400 nm, and may be about 100 nm in some cases. In many embodiments, the microbubble dispersion is able to remain dispersed at atmospheric pressure for at least 15 minutes.

Once sheared, the resulting phthalic acid derivative/alcohol solution exits HSD 140 via line 118 and feeds into vessel 110, as illustrated in FIG. 1. As a result of the intimate mixing of the reactants prior to entering vessel 110, a significant portion of the chemical reaction may take place in HSD 140, with or without the presence of a catalyst. Accordingly, in some embodiments, reactor/vessel 110 may be used primarily for heating and separation of volatile reaction products from the phthalic acid diester product. Alternatively, or additionally, vessel 110 may serve as a primary reaction vessel where most of the phthalic acid diester product is produced. Vessel/reactor 110 may be operated in either continuous or semi-continuous flow mode, or it may be operated in batch mode. The contents of vessel 110 may be maintained at a specified reaction temperature using heating and/or cooling capabilities (e.g., cooling coils) and temperature measurement instrumentation. In and embodiment, vessel 110 may be a reactive distillation column. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously.

The reaction may proceed under temperature and pressure conditions commonly employed in such catalytic esterification reactions. There is no particular restriction as to the reaction conditions. However, the pressure is selected usually within a range of from about atmospheric pressure to 10 MPa, alternatively from about 2 to about 4 MPa, and the reaction temperature may be within a range of from about 15° C. to about 350° C., alternatively from about 75° C. to about 150° C.

As discussed above, the phthalic acid derivative supplied to line 112 may be any phthalic acid derivative known by those of skill in the art to produce phthalic acid diester. Examples include without limitation, phthalic acid, phthalate anhydride, and the like. Sources of the derivatives may be from any suitable source. Likewise, the alcohol for the reaction may come from any suitable source. For example, the alcohol may be the result of ethylene hydration, a Fischer-Tropsch process, or a fermentation process.

The reaction solution may be further processed prior to entering vessel 110 if desired. The contents of the vessel are stirred continuously or semi-continuously, the temperature of the reactants is controlled (e.g., using a heat exchanger), and the fluid level inside vessel 110 is regulated using standard techniques. The reaction may occur either continuously, semi-continuously or batch wise, as desired for a particular application. Any by-products that are produced may exit reactor 110 via line 117. This exit stream 117 may comprise water formed from the esterification reaction and may be withdrawn from water outlet stream 117.

The combined distillable products may then be separated in a series of distillation steps to give phthalic acid diester, the product; unconverted acetaldehyde, for recycle; light ends which can be used for fuel; a mixture of phthalic acid diester and ethanol, and a by-product, acetaldehyde diethyl acetal, which can be recovered for sale or hydrolyzed for recovery of acetaldehyde and ethanol.

Dibutyl phthalate may be produced from the above disclosed process. Phthalic anhydride and butanol may be mixed in a high shear device to form a reaction mixture stream. The reaction mixture may include a catalyst to form a slurry reaction mixture or the reaction mixture may be flowed through a fixed or fluidized bed reactor. The reaction is shown below:

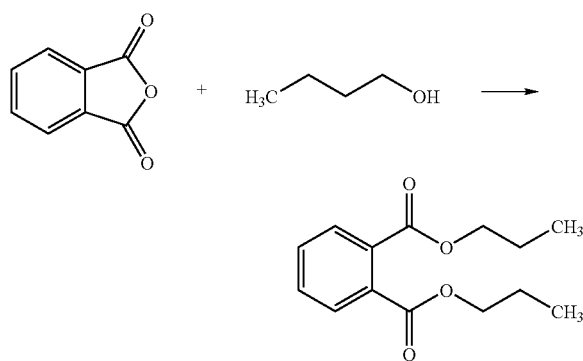

Other known methods of producing phthalic acid diester may be also used with a high shear device 140.

Catalyst. The process can take place in the presence of a catalyst or without catalyst. The catalysts are generally strong mineral acids such as sulfuric acid or hydrochloric acid, and aromatic sulfonic acids, such as benzene sulfonic acid, para toluene sulfonic acid, and mixtures thereof. In addition, aluminum chloride, zinc chloride, and Lewis acids such as boron trifluoride are also useful catalysts as are aliphatic sulfonic acids. In addition, amphoteric-based compounds have been used as catalysts, for example, divalent tin oxide, divalent tin oxylate, metallic tin, bismuth oxide and mixtures thereof. These amphoteric-based catalysts have been, however, mostly used in batch processes for the production of phthalic esters.

Recently, lower alkyl titanium esters and lower alkyl zirconium esters have been utilized as catalysts for the production of phthalic esters in both batch and continuous processes. Generally said ester catalysts contain about 3 to about 8 carbon atoms in the alkyl group. Useful examples of the titanium esters are isopropyl titanate, 2-ethyl hexyl titanate and n-butyl titanate.

If a catalyst is used to promote the reaction, it may be introduced into the vessel via line 115, as an aqueous or nonaqueous slurry or stream. Alternatively, or additionally, catalyst may be added elsewhere in the system 100. For example, catalyst slurry may be injected into line 121.

A strong acid ion exchange resin such as Rohm and Haas A-16 can be used in the reactor 110. The catalyst is employed in an amount sufficient to initiate and maintain reaction. A homogeneous catalyst liquid phase or a pump around bed, which enable the liquid to be pumped across a packed bed of solid catalyst 142 can be employed within the scope of the method. Catalyst may be fed into reactor 110 through catalyst feed stream 115.

As mentioned above, stream 118 may optionally enter fluidized or fixed bed 142 in lieu of a slurry catalyst process. However, in a slurry catalyst embodiment, high shear outlet stream 118 may directly enter reactor 110 for phthalic acid diester production. Where a slurry based catalyst is utilized, reaction is more likely to occur at points outside the reactor (110) shown in FIG. 1. Nonetheless a discrete reactor is often desirable to allow for increased residence time, agitation and heating and/or cooling. When fixed bed catalyst is utilized, the reactor becomes the main location for the reaction to occur due to the presence of catalyst. The reaction stream may be maintained at the specified reaction temperature, using cooling coils in the reactor 110 to maintain reaction temperature.

Multiple Pass Operation. In the embodiment shown in FIG. 1, the system is configured for single pass operation, wherein the output from vessel 110 goes directly to further processing for recovery of phthalic acid diester product. In some embodiments it may be desirable to pass the contents of vessel 110, or a liquid fraction containing phthalic acid diester product, unreacted alcohol and/or phthalic acid diester derivative, through HSD 140 during a second pass. In this case, line 116 is connected to line 121 via dotted line 120, and the recycle stream from vessel 110 is pumped by pump 105 into line 113 and thence into HSD 140. Additional alcohol may be injected via line 122 into line 113, or it may be added directly into the high shear device (not shown).

Multiple High Shear devices. In some embodiments, two or more high shear devices like HSD 140, or configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 110 may be omitted. In some embodiments, multiple high shear devices 140 are operated in parallel, and the outlet dispersions therefrom are introduced into one or more vessel 110.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of making a phthalic acid diester comprising:
   a) forming a mixture comprising an alcohol and at least one component selected from the group consisting of phthalic acid and phthalic acid derivatives;
   b) subjecting the mixture to a shear rate of greater than 20,000 s$^{-1}$ by introducing the mixture into an external high shear device comprising at least one generator comprising a toothed rotor and a complementarily-shaped stator separated by a shear gap width in the range of from about 0.025 mm to about 10.0 mm, wherein said external high shear device is configured to produce a local pressure of at least about 1034.2 MPa at said rotor tip; and
   c) extracting a high-shear treated stream from the high shear device.

2. The method of claim 1, wherein the high shear treated stream comprises gas bubbles or liquid droplets having an average diameter of less than 400 nm.

3. The method of claim 2, wherein the high shear treated stream comprises gas bubbles or liquid droplets having an average diameter of no more than about 100 nm.

4. The method of claim 1 wherein the mixture further comprises a catalyst and wherein the catalyst is selected from the group consisting of sulfuric acid, hydrochloric acid, aromatic sulfonic acids, benzene sulfonic acid, p-toluene sulfonic acid, and combinations thereof.

5. The method of claim 1, wherein (b) comprises subjecting said reactant stream to high shear mixing at a tip speed of at least about 20 m/sec.

6. The method of claim 1, wherein forming said dispersion comprises an energy expenditure of at least about 1000 W/m$^3$.

7. The method of claim 1 further comprising introducing the high-shear treated stream into a reactive distillation column.

8. The method of claim 1 wherein the phthalic acid diester has the formula:

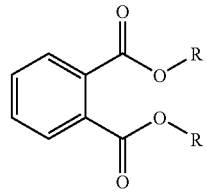

wherein R is an alkyl group having from 1 to 10 carbon atoms and R may be branched or unbranched.

9. The method of claim 1 wherein the alcohol comprises a saturated alcohol having from 1 to 10 carbon atoms.

10. The method of claim 5 wherein the tip speed is greater than 40 m/s.

11. The method of claim 1 wherein the mixture comprises an excess of alcohol.

12. The method of claim 1 further comprising d) introducing the high-shear treated stream into a vessel.

13. The method of claim 12 wherein the vessel comprises at least one catalyst selected from the group consisting of finely divided tin, tin(II)oxide, tin(II)oxalate, titanate esters and zirconium esters.

14. The method of claim 1 wherein the high shear treated stream comprises gas bubbles or liquid droplets having an average diameter of less than 1 μm.

* * * * *